(12) United States Patent
Kapil

(10) Patent No.: US 9,180,034 B1
(45) Date of Patent: Nov. 10, 2015

(54) DEVICE FOR ASSISTING WEIGHT CONTROL

(71) Applicant: Sanjiv Kapil, Lake Mary, FL (US)

(72) Inventor: Sanjiv Kapil, Lake Mary, FL (US)

(*) Notice: Subject to any disclaimer, the term of this patent is extended or adjusted under 35 U.S.C. 154(b) by 316 days.

(21) Appl. No.: 13/733,651

(22) Filed: Jan. 3, 2013

Related U.S. Application Data

(60) Provisional application No. 61/684,926, filed on Aug. 20, 2012.

(51) Int. Cl.
   *A61G 13/12*  (2006.01)
   *A61F 5/00*  (2006.01)

(52) U.S. Cl.
   CPC ..................... *A61F 5/0006* (2013.01)

(58) Field of Classification Search
   USPC .............. 128/848, 859–862; 433/6–7; 604/77
   See application file for complete search history.

(56) References Cited

U.S. PATENT DOCUMENTS

| | | | |
|---|---|---|---|
| 2,849 A | 11/1842 | Foster | |
| 5,181 A | 7/1847 | Stuart | |
| 4,471,771 A * | 9/1984 | Steven et al. | 128/859 |
| 4,738,259 A | 4/1988 | Brown | |
| 4,842,519 A | 6/1989 | Dworkin | |
| 6,138,679 A * | 10/2000 | Renders et al. | 128/897 |
| 2003/0059737 A1 | 3/2003 | Hall | |
| 2003/0075186 A1* | 4/2003 | Florman | 128/869 |
| 2005/0016547 A1* | 1/2005 | Mousselon et al. | 128/861 |
| 2007/0298366 A1 | 12/2007 | Rothstein | |
| 2009/0035729 A1 | 2/2009 | Pele | |
| 2010/0109876 A1* | 5/2010 | Schmid-Schonbein et al. | 340/573.1 |
| 2010/0288287 A1 | 11/2010 | Pines | |
| 2012/0109051 A1 | 5/2012 | Harrell | |

* cited by examiner

*Primary Examiner* — Ophelia A Hawthrone
(74) *Attorney, Agent, or Firm* — Brian S. Steinberger; Law Offices of Brian S. Steinberger, P.A.

(57) ABSTRACT

Devices and methods for assisting weight control where the device is inserted into the mouth of a patient between opposing rear molar teeth. The inserted devices cause an increase in resistance to chewing, which then slows eating by the person. The devices can include elastic bands, magnets, shock absorbers, combinations, thereof and sensors for detecting strength and frequency of chewing.

14 Claims, 11 Drawing Sheets

Fig. 11A

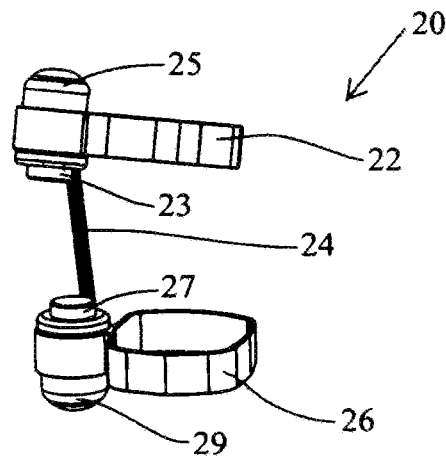
Fig. 5
Fig. 6
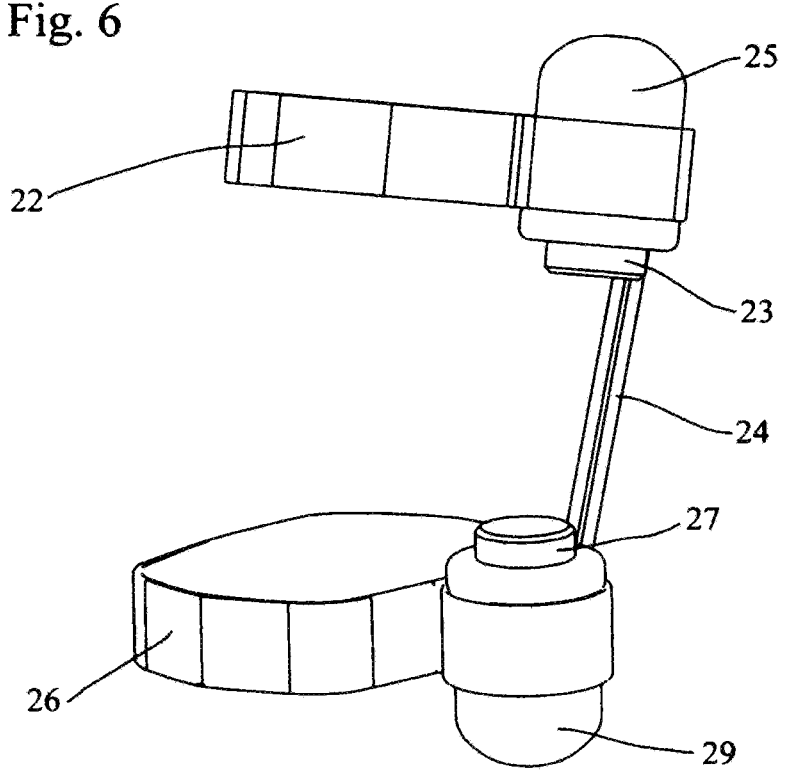

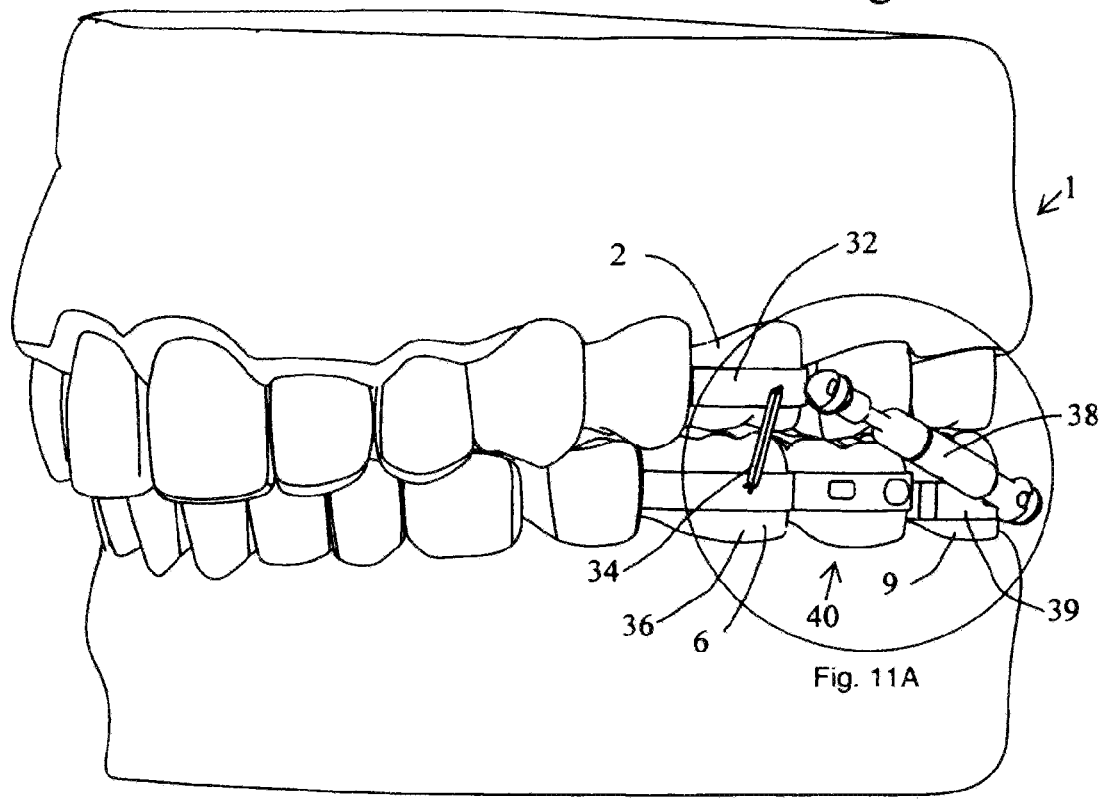
Fig. 11
Fig. 11A
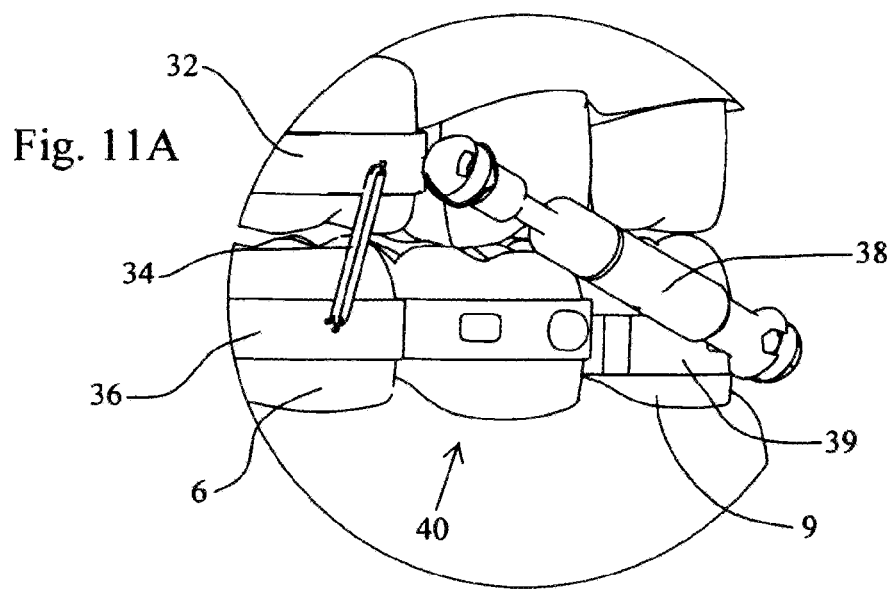
Fig. 11A

DEVICE FOR ASSISTING WEIGHT CONTROL

This invention claims the benefit of priority to U.S. Provisional Patent Application Ser. No. 61/684,926 filed Aug. 20, 2012.

FIELD OF INVENTION

This invention relates to weight loss, and in particular to devices and methods of providing a device for assisting weight control where the device is inserted into the mouth of a patient between opposing molar teeth which causes an increase in resistance which increases work for chewing, which then slows eating by the person.

BACKGROUND AND PRIOR ART

Obesity is a major health risk factor in the world, and in particular in the United States. U.S. DEPARTMENT OF HEALTH AND HUMAN SERVICES, National Center for Health Statistics estimates this to be about 35.7 per cent of the US population. Obesity can lead to hypertension, diabetes, heart attacks, osteoarthritis amongst various medical conditions.

A study from the Centers for Disease Control and Prevention (CDC) and Research Triangle Institute (RTI International) released in July 2009 estimated that obesity and obesity-related health conditions cost almost ten percent of annual medical spending in the US, totaling $147 billion in 2008. This is a condition which requires significant intervention at a national and an individual level.

Numerous ways exist to address this condition such as diet, weight loss drugs, psychotherapy, exercise, change in life style and surgery. Various types of medications used for this process include phenteramine, amphetamine and FDA approved lorcaserin.

A common surgical procedure can include gastric bypass and gastric banding. These medications and surgical procedures can have long term effects and complications.

A medical condition called giant cell arteritis can lead to decreased blood flow to the muscles for chewing. This condition leads to fatigue while trying to chew similar to as any muscle would if it did not get enough blood supply. This condition invariably leads to weight loss.

Various types of elaborate systems have also been proposed over the years. See for example, U.S. Published Patent Application 2010/0109876 to Schmid-Schonbein et al. which describes elaborate devices, systems and methods to control caloric intake where sensors can be attached to a patient's teeth and personalized feedback can occur. However, this device and system requires computers where feedback which only instructs the patient to eat slower, and does not physically restrict their chewing.

Thus, the need exists for solutions to the above problems with the prior art.

SUMMARY OF THE INVENTION

A primary objective of the present invention is to provide an oral device and method that increases the work and energy in chewing and consequently an obstacle to prolonged mastication.

A secondary objective of the present invention is to provide a device and method for assisting weight control where the device is inserted into the mouth of a patient between opposing molar teeth which causes an increase in resistance to increase resistance to chewing, which then slows eating by the person.

The present invention provides devices, and methods to control the rate as well as total calorie consumption at a meal, and consequently body weight of a user, by encouraging the user to chew slower and for longer periods of time, adjusting a time interval between bites, which in essence lowers caloric intake.

The present invention assists in retraining of eating habits towards a lifetime of controlled calorie consumption. Over time, the user's consumption patterns or eating habits are altered, resulting in a desired outcome such as weight loss.

A mouth insertion device for assisting in weight control, can include an elastic band adaptable to be mounted in a back of the mouth between an upper jaw and lower jaw, the elastic insert for increasing resistance of the upper jaw and the lower jaw during chewing action.

The device can further include an upper strap attached to an upper molar, and a lower strap attached to a lower molar, with the elastic band attached to the both the upper strap and the lower strap.

The device can further include a second elastic band adaptable to be mounted in a back of the mouth between an upper jaw and lower jaw, a second upper strap attached to a second upper molar, a second lower strap attached to a second lower molar, with the second elastic band attached to the both the second upper strap and the second lower strap.

The device can further include a first magnet attached to the upper molar strap, and a second magnet attached to the lower molar strap, the first magnet and the second magnet having identical poles so that the first magnet and the second magnet having opposing forces to one another.

The device can further include a shock absorber having an upper end attached to the upper molar strap, and a second end attached to a second lower molar strap, the second molar strap being attached to a second molar tooth. The shock absorber can include a telescoping piston.

The device can include the combination of a first magnet attached to the upper molar strap, a second magnet attached to the lower molar strap, the first magnet and the second magnet having identical poles so that the first magnet and the second magnet having opposing forces to one another, and a shock absorber having an upper end attached to the upper molar strap, and a second end attached to a second lower molar strap, the second molar strap being attached to a second molar tooth.

The device can include sensors for detecting strength and chewing frequency data and for remotely transmitting the data to a remote location.

Methods of mounting and using the devices are included.

Further objects and advantages of this invention will be apparent from the following detailed description of the presently preferred embodiments which are illustrated schematically in the accompanying drawings.

BRIEF DESCRIPTION OF THE FIGURES

FIG. 5 is a side perspective view of a magnet and elastic band embodiment.

FIG. 6 is another side perspective view of a magnet and elastic band embodiment.

FIG. 11 is a side view of the shock absorber with elastic band and straps installed in a mouth.

FIG. 11A is an enlarged view of the installed shock absorber and elastic band of FIG. 11.

DESCRIPTION OF THE PREFERRED EMBODIMENTS

Figure 1:
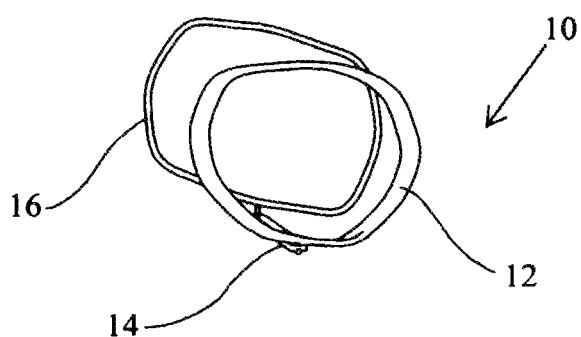
FIG. 1 is a lower perspective view of an elastic band and molar straps embodiment.

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

A listing of components will now be described.
1. Mouth
2. upper molar
6. lower molar
10. elastic band embodiment
12. upper molar strap
14. elastic band
16. lower molar strap
20. magnet and elastic band embodiment
22. upper molar strap
23. upper magnet
25. upper housing for upper magnet
24. elastic band
26. lower molar strap
27. lower magnet
29. lower housing for lower magnet
30. shock absorber and elastic band embodiment
32. upper molar strap
34. elastic band
36. lower molar strap
38. shock absorber with piston
39. second lower molar strap
40. strap with mastication sensor embodiment
42. strap
44. strength sensor
46. frequency sensor
50. hybrid embodiment The novel oral device increases the work and energy in chewing and consequently is an obstacle to prolonged mastication. The invention can have similar results to stapling or banding the stomach and lead to decreased eating. With the invention, prolonged chewing would cause jaw muscle fatigue and satiation.

Elastic Band Embodiment

Figure 2:
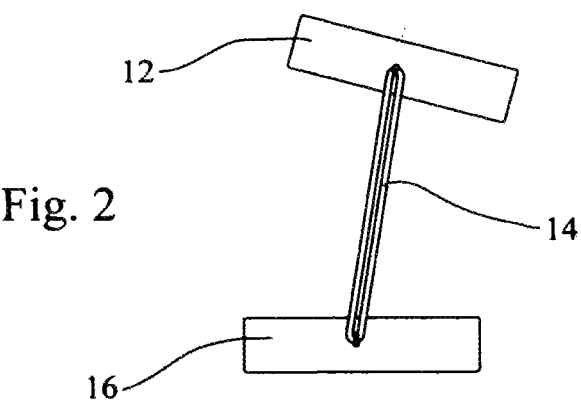
FIG. 2 is a side view of the elastic band and molar straps embodiment of FIG. 1.
Figure 3:
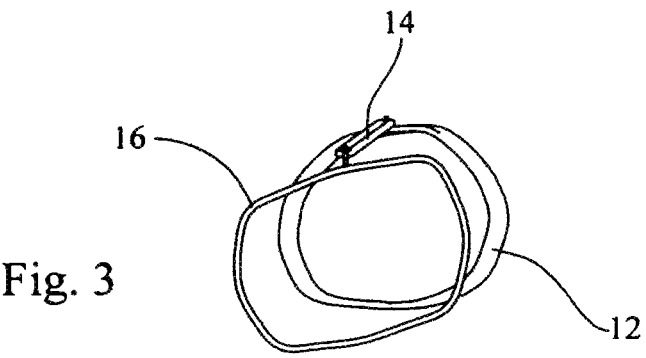
FIG. 3 is an upper perspective view of the elastic band and molar straps embodiment of FIG. 1.
Figure 4A:
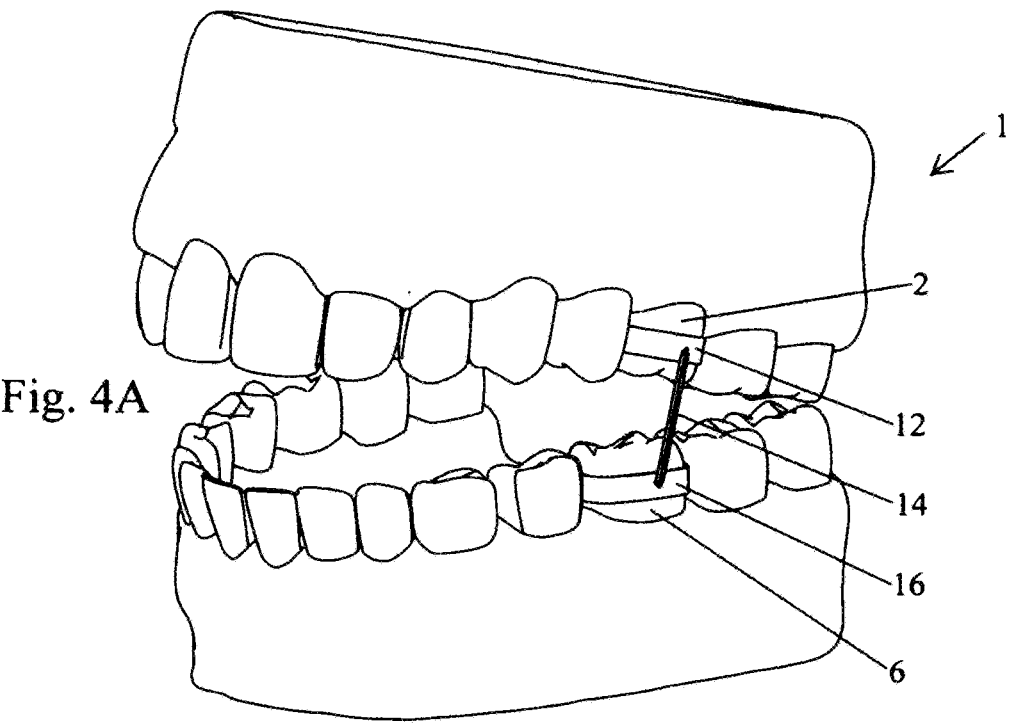
FIG. 4A is a perspective view of the band and straps of the preceding embodiment installed in an open mouth.
Figure 4B:
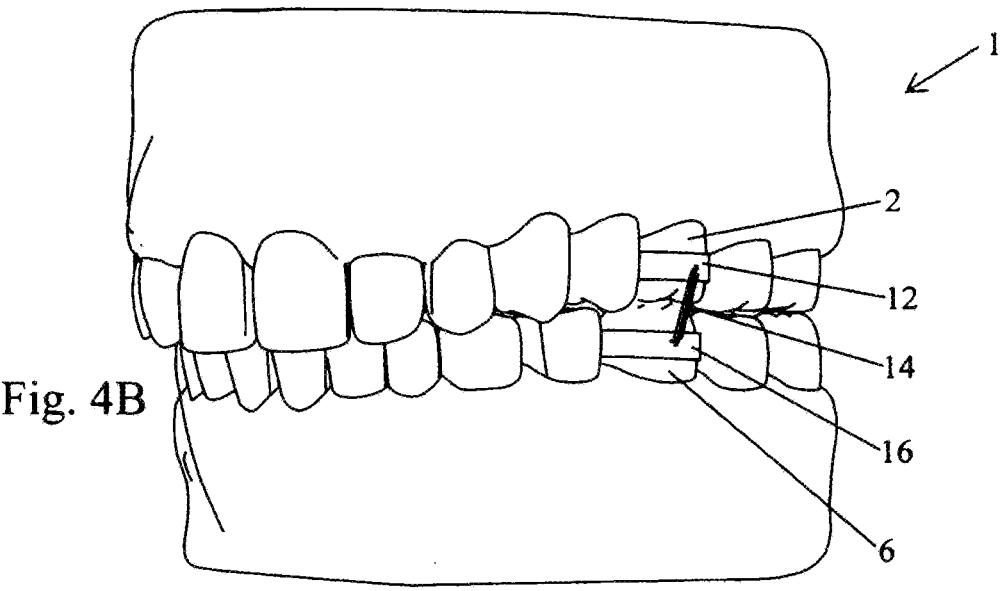
FIG. 4B is a perspective view of the installed band and straps of FIG. 4A in a closed mouth.

FIG. 1 is a lower perspective view of an elastic band 14 and molar straps 12, 16 embodiment 10. FIG. 2 is a side view of the elastic band 14 and molar straps 12, 16 embodiment 10 of FIG. 1. FIG. 3 is an upper perspective view of the elastic band 14 and molar straps 12, 16 embodiment 10 of FIG. 1. FIG. 4A is a perspective view of the band 14 and straps 12, 16 of the preceding embodiment 10 installed in an open mouth 1. FIG. 4B is a perspective view of the installed band 14 and straps 12, 16 of FIG. 4A in a closed mouth 1.

Referring to FIGS. 1-4B, the upper molar strap 12 can be strapped about an upper left molar tooth 2 with the lower molar strap 16 strapped to a lower left molar tooth 6. A second set embodiment 10 can be similarly mounted to an upper right molar tooth and a lower left molar tooth. The straps 12, 16 can be formed from material such as plastic, elastomer, and the like for tightly being attached and anchored to each molar tooth. The elastic band 14 can be similar to a rubber band used with orthodontic braces having an elasticity when stretched which causes the band to retract back to its' original unstretched position.

The elastic band 14 increases resistance of opening the mouth 1 during chewing. With the installed elastic band 14, there is an increased resistance every time the mouth would be opened during chewing.

Magnet and Elastic Band Embodiment

Figure 7A:
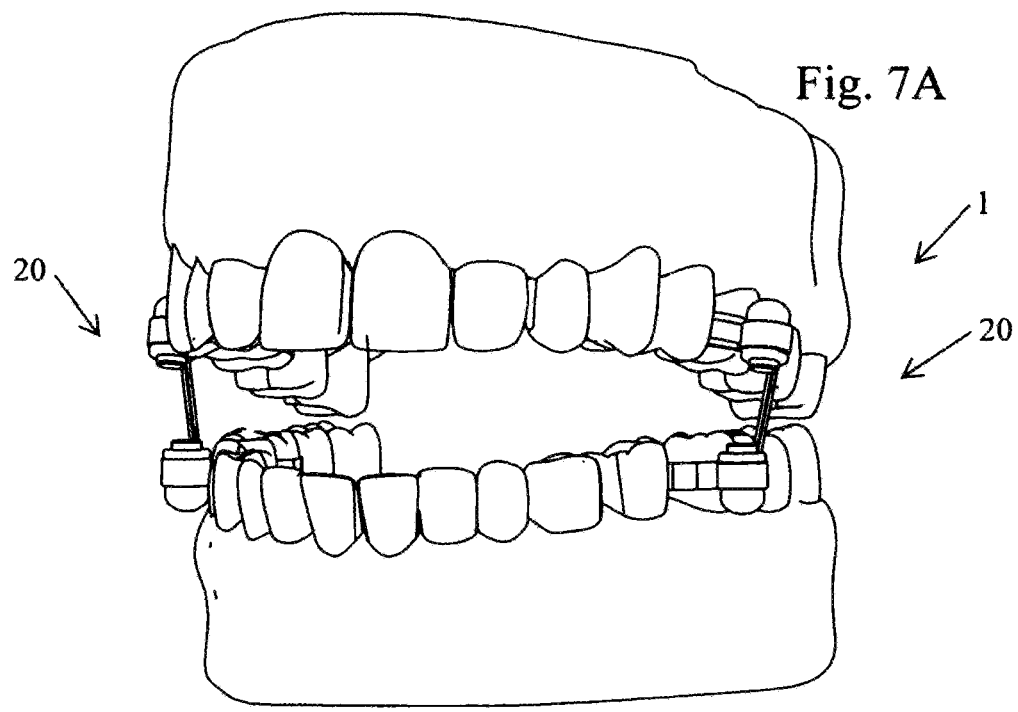
FIG. 7A is a front perspective view of the magnet and band embodiment of FIGS. 5-6 installed with mouth in an open position.
Figure 7B:
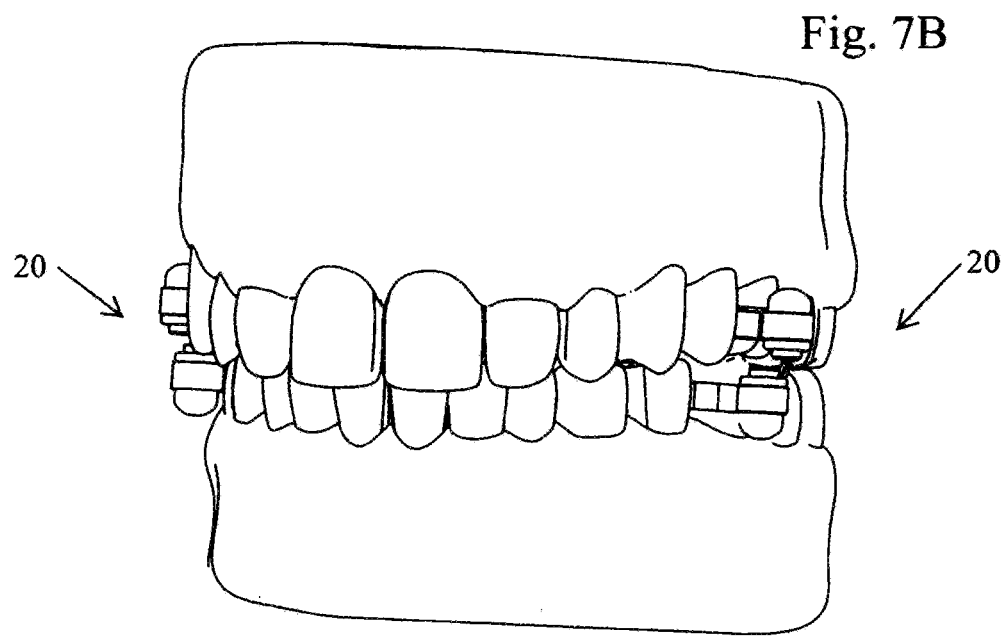
FIG. 7B is another front view of the installed magnet and band embodiment of FIG. 7A with mouth in a closed position.
Figure 7C:
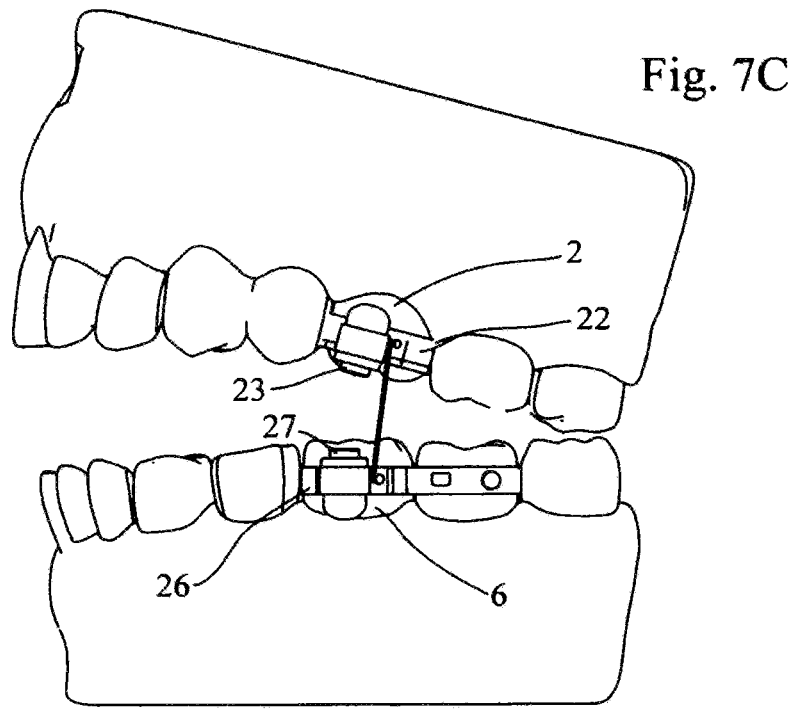
FIG. 7C is a side view of the magnet and band embodiment installed in a mouth of FIG. 7A in an open position.
Figure 7D:
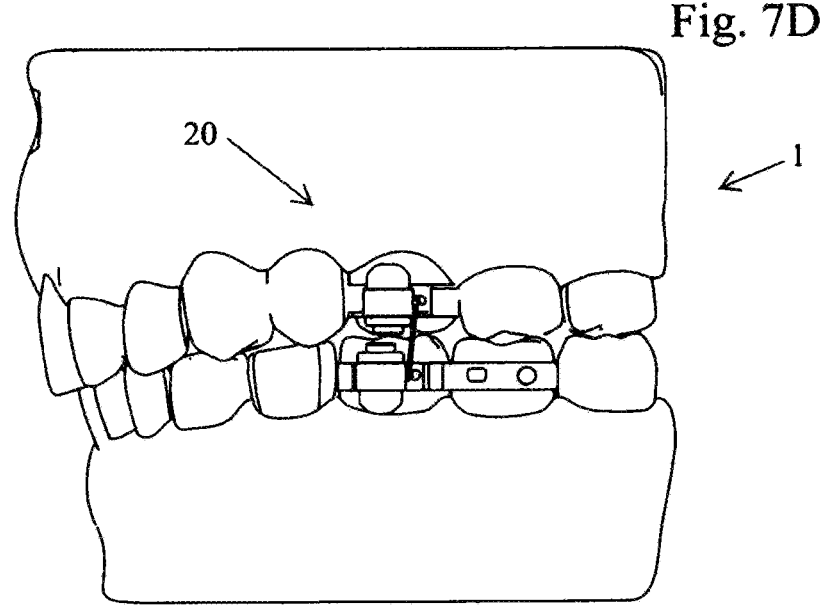
FIG. 7D is a side view of the magnet and band embodiment installed in a mouth of FIG. 7B in a closed position.

FIG. 5 is a side perspective view of a magnet 23, 27 and elastic band 24 embodiment 20. FIG. 6 is another side perspective view of a magnet 23, 27 and elastic band 24 embodiment 20. FIG. 7A is a front perspective view of the magnet 23, 27 and band 24 embodiment 20 of FIGS. 5-6 installed with mouth 1 in an open position. FIG. 7B is another front view of the installed magnet 23, 27 and band 24 embodiment 20 of FIG. 7A with mouth 1 in a closed position. FIG. 7C is a side view of the magnet 23, 27 and band 24 embodiment 20 installed in a mouth 1 of FIG. 7A in an open position. FIG. 7D is a side view of the magnet 23, 27 and band 24 embodiment 20 installed in a mouth 1 of FIG. 7B in a closed position.

Referring to FIGS. 5-7D, an upper molar strap 22 with a first magnet 23 can be strapped about an upper left molar 2 and a lower molar strap 26 with a second magnet 27 having a similar pole as the first magnet can be strapped about a lower left molar 6. An identical similar pole magnets and elastic band embodiment 20 can be mounted to an upper right molar and a lower right molar, respectively. An elastic band 24 can have ends attached to the upper molar strap 22 and lower molar strap 26. An upper housing 25 attached to the upper molar strap 22 can have a first magnet 23 mounted in a lower side. A lower housing 29 attached to the lower molar strap 26 can have a second magnet 27 with a similar pole to the first magnet 23 mounted in an upper side. The first and second magnets 23, 27 can both be positive so as to cause opposing forces therebetween.

The magnets 23, 27 can be such as those shown and described in U.S. Published Patent Applications: 2003/0075186 to Florman and 2003/0059737 to Hall, which are both incorporated by reference.

Replaceable magnets having similar poles 23, 27 can be inserted on the housings 25, 29 for variable levels of resistance. The replaceable magnets 23, 27 can offer different levels of resistance. The elastic band 24 can also offer an extra level of resistance and can also limit the mouth opening between the lower jaw and the upper jaw to add further work during chewing.

Additionally, small replaceable batteries inside the respective housings 25, 29 can be attached to the magnets 23, 27 to further increase and adjust the opposing forces of the similar pole magnets 23, 27. The magnets can include ferromagnets or electromagnets with an inserted battery. The strength of the magnet can be electronically controlled with signals from outside as well as switched on and off as needed for meals and kept off otherwise. The magnets can also be recharged that can be recharged remotely by induction, and the like, without having to remove the batteries from their respective housings.

Shock Absorber and Elastic Band

Figure 8:
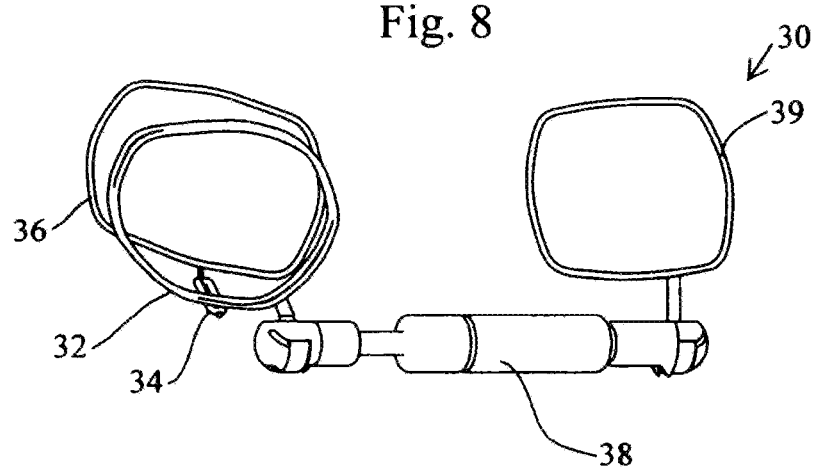
FIG. 8 is a perspective view of another embodiment of a shock absorber with elastic band and molar straps embodiment.
Figure 9:
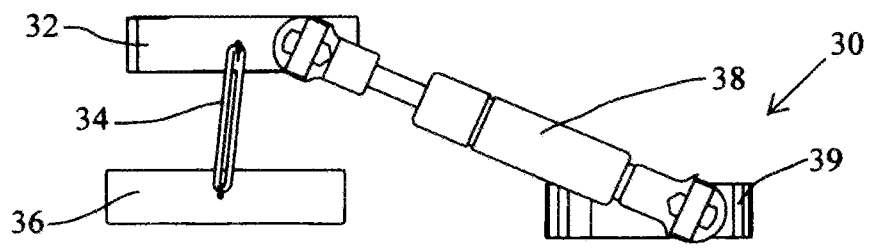
FIG. 9 is a side view of the shock absorber with elastic band and molar straps embodiment of FIG. 8.
Figure 10:
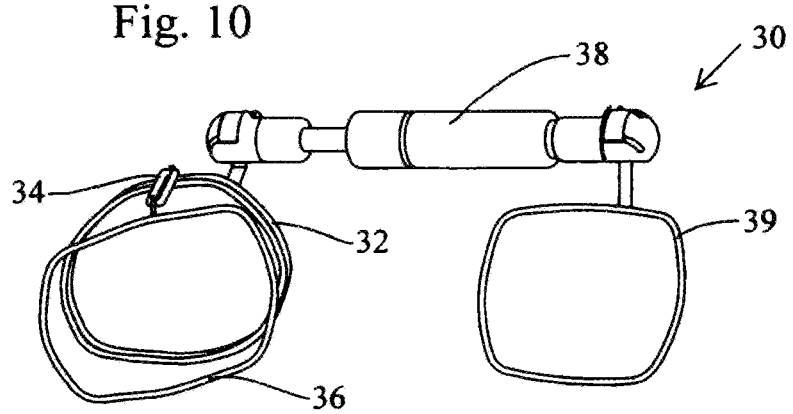
FIG. 10 is another perspective view of the shock absorber with elastic band and molar straps embodiment of FIG. 8.
Figure 11B:
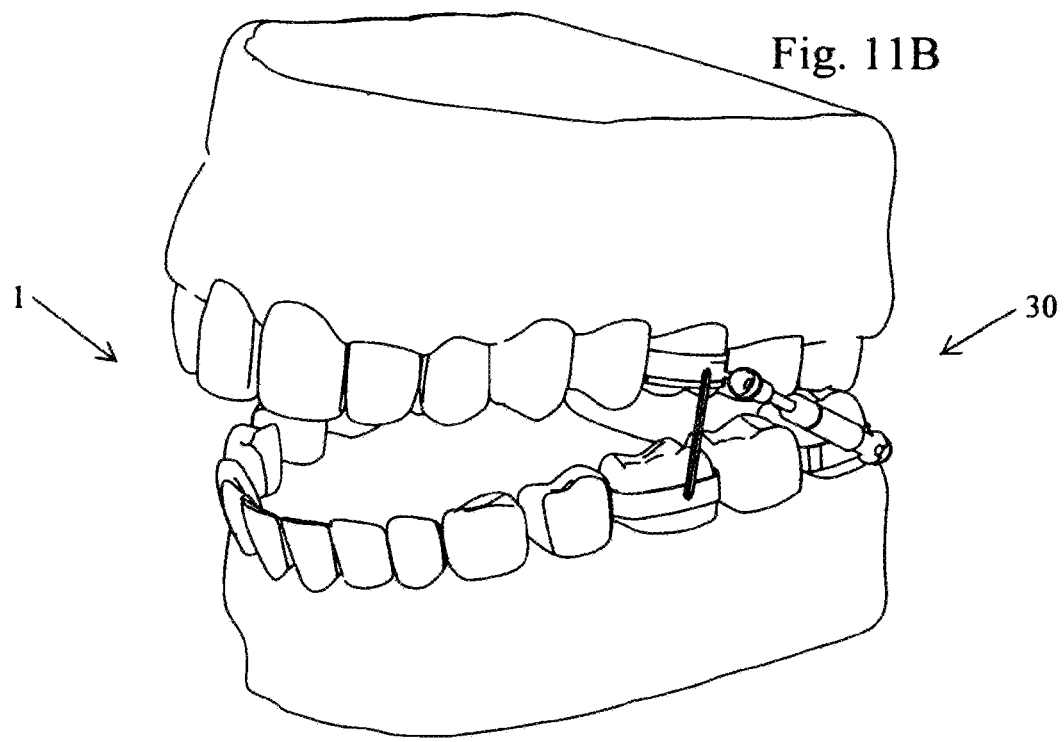
FIG. 11B is a perspective view of the installed shock absorber and elastic band of FIG. 11 in an open mouth.
Figure 11C:
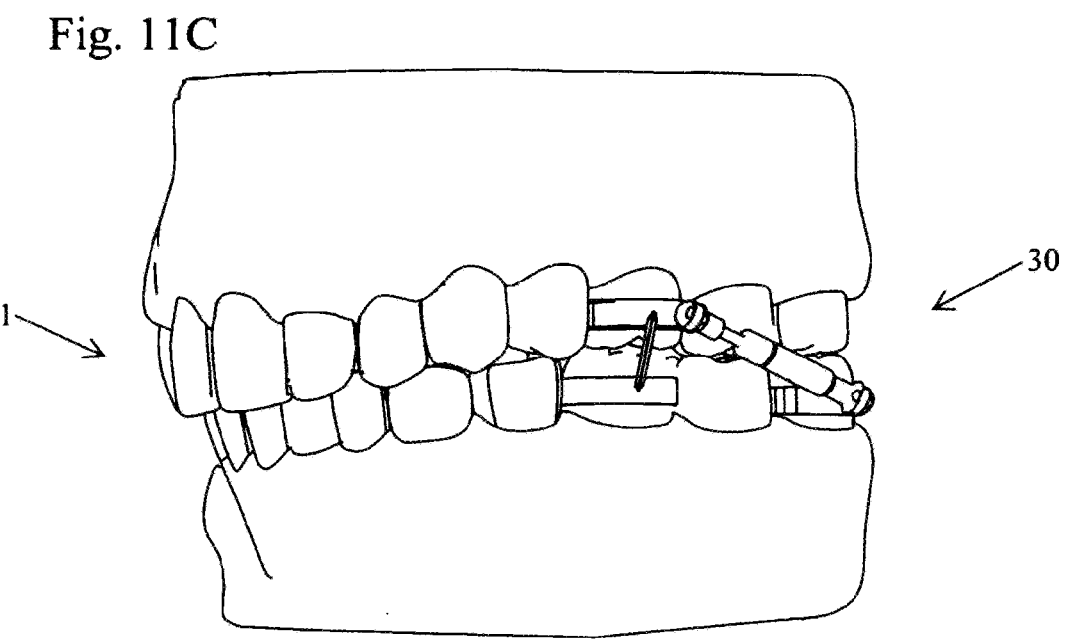
FIG. 11C is a perspective view of the installed shock absorber and elastic band of FIG. 11 in a closed mouth.

FIG. 8 is a perspective view of another embodiment 30 of a shock absorber 38 with elastic band 34 and molar straps 32, 36, 39 embodiment 30. FIG. 9 is a side view of the shock absorber 38 with elastic band 34 and molar straps 32, 36, 39 embodiment 30 of FIG. 8. FIG. 10 is another perspective view of the shock absorber 38 with elastic band 34 and molar straps 32, 36, 39 embodiment 30 of FIG. 8. FIG. 11 is a side view of the shock absorber 38 with elastic band 34 and straps 32, 36, 39 installed in a mouth 1. FIG. 11A is an enlarged view of the installed shock absorber 38 and elastic band 34 of FIG. 11. FIG. 11B is a perspective view of the installed shock absorber 38 and elastic band 34 of FIG. 11 in an open mouth 1. FIG. 11C is a perspective view of the installed shock absorber 38 and elastic band 34 of FIG. 11 in a closed mouth 1.

Referring to FIGS. 8-11C, a first shock absorber and elastic band embodiment 30 can include an upper molar strap 32 can be strapped to an upper left molar 2 and a lower molar strap 36 can be attached to a lower left molar 6. A second shock absorber and elastic band embodiment 30 can be similarly attached to an upper right molar and a lower right molar. An elastic band 34 can have ends attached to the upper molar strap 32 and the lower molar strap 36. A shock absorber 38 having one side with a piston which telescoping inserts in and out of a second side can be attached to the upper molar strap 32 and to a second lower molar strap 39. The second lower strap can be attached to a second lower molar 9 behind the first lower molar 6. The combination of the elastic band 34 and shock absorber with piston 38 can offer different levels of resistance, and can also limit the mouth opening between the lower jaw and the upper jaw to add further work during chewing.

Mastication Strap Sensor Embodiment

Figure 12:
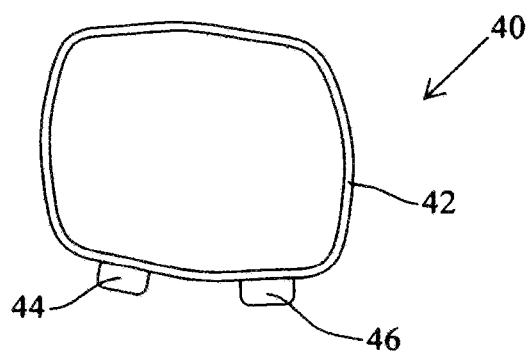
FIG. 12 is a top view of a band with sensors for sensing strength and frequency of the mastication of a chewer.
Figure 13:
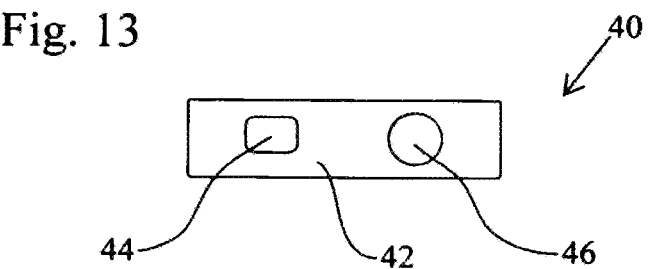
FIG. 13 is a side view of the band with sensors of FIG. 12.
Figure 14:
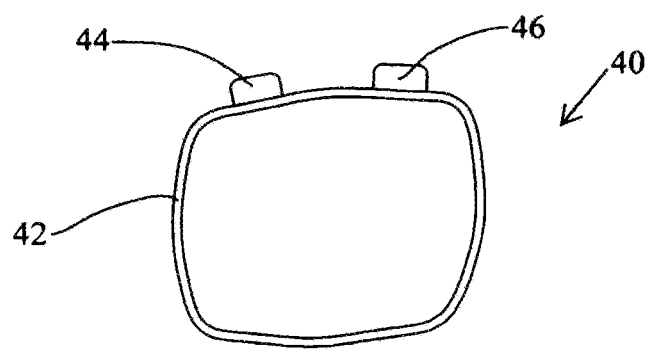
FIG. 14 a bottom view of the band with sensors of FIG. 12.

FIG. 12 is a top view of a band embodiment 40 with sensors 44, 46 for sensing strength and frequency (similar to a pedometer) of the mastication of a chewer. FIG. 13 is a side view of the band 40 with sensors 44, 46 of FIG. 12. FIG. 14 a bottom view of the band 40 with sensors 44, 46 of FIG. 12. A strap 42 can have a sensor for sensing strength 44 and frequency 46 of a chewer. The strap 42 can be strapped about a molar tooth adjacent to either the upper and lower molar teeth which the resistance devices of the preceding figures are mounted to.

Hybrid with Elastic Band, Magnets and Shock Absorber

Figure 15A:
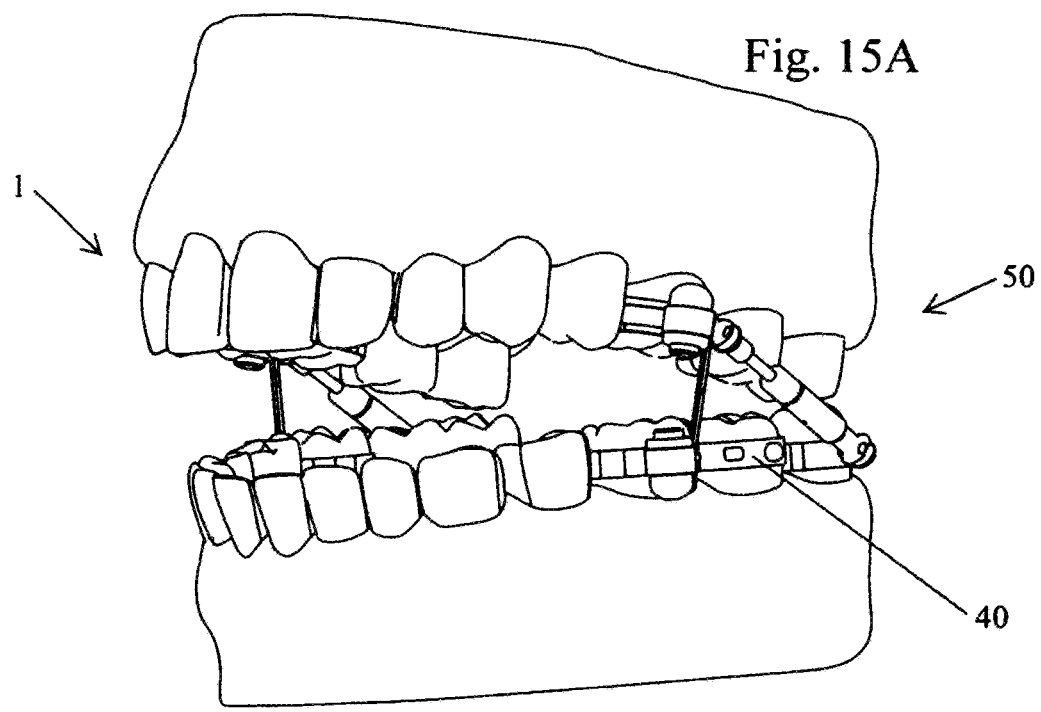
FIG. 15A is a perspective view of an installed hybrid embodiment of magnets, elastic band, shock absorber and sensors installed in an open mouth.
Figure 15B:
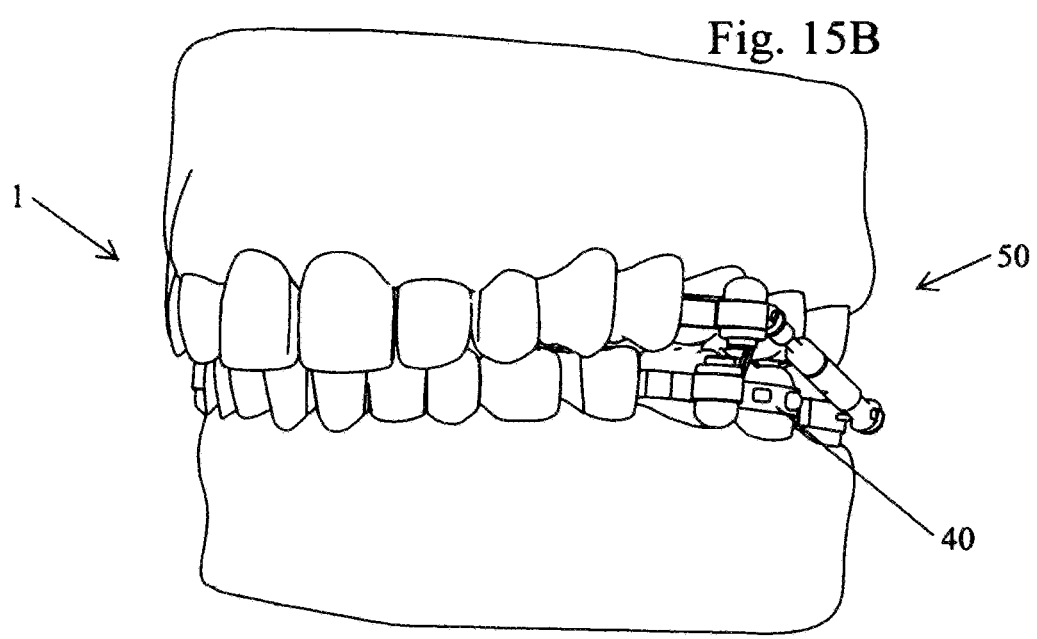
FIG. 15B is another perspective view of the installed hybrid embodiment of FIG. 15A in a closed mouth.
Figure 15C:
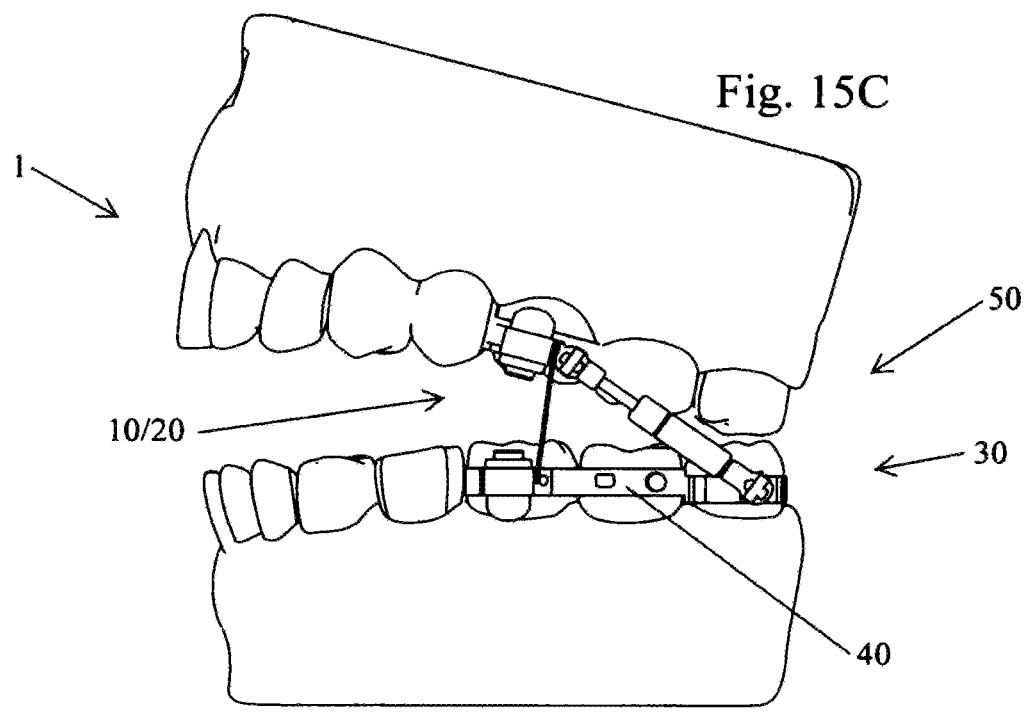
FIG. 15C is a side view of the installed hybrid embodiment of FIG. 15A in an open mouth.
Figure 15D:
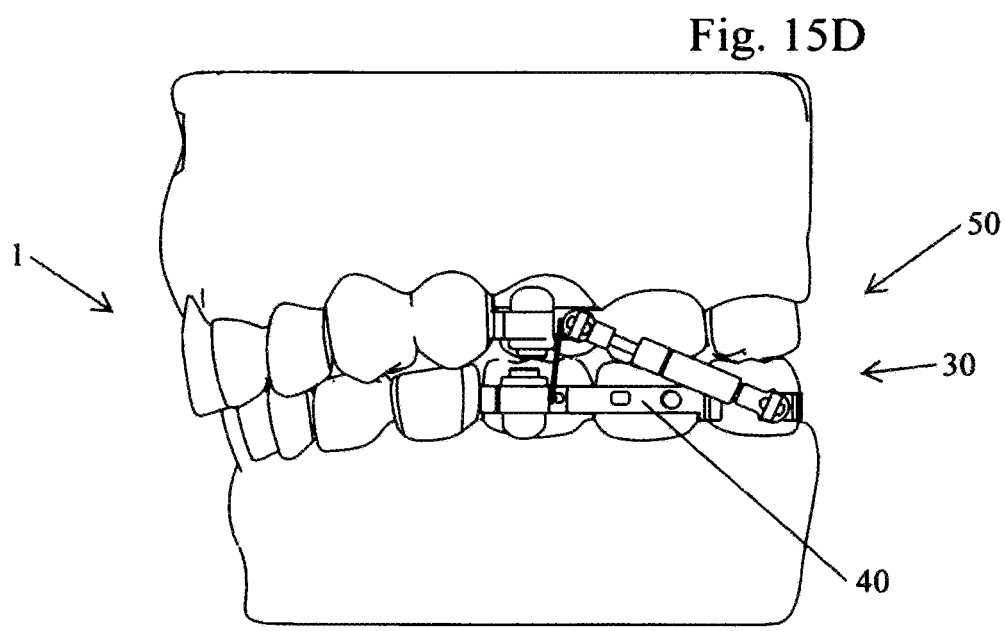
FIG. 15D is a side view of the installed hybrid embodiment of FIG. 15B in a closed mouth.

FIG. 15A is a perspective view of an installed hybrid embodiment 50 of magnet embodiment 20, elastic band embodiment 10, shock absorber embodiment 30 and sensors 40 installed in an open mouth 1. FIG. 15B is another perspective view of the installed hybrid embodiment 50 of FIG. 15A in a closed mouth 1. FIG. 15C is a side view of the installed hybrid embodiment 50 of FIG. 15A in an open mouth 1. FIG. 15D is a side view of the installed hybrid embodiment 50 of FIG. 15B in a closed mouth 1. The hybrid embodiment 50 can combine an elastic band embodiment 10, magnet embodiment 20 and shock absorber embodiment 30 together with sensor embodiment 40. The combination of the elastic band embodiment 10, magnet embodiment 20 and shock absorber embodiment 30 can offer different levels of resistance, and can also limit the mouth opening between the lower jaw and the upper jaw to add further work during chewing.

The strength sensor 44 and frequency sensors 46 can send data remotely and wirelessly to a receiver such as a smart phone and the like, such as but not limited to an IPHONE®, GALAXY®, BLACKBERRY®, and the like. Collected data can be displayed to show the chewing strength and frequency when using and not using the installed embodiments. The collected data can be used by professionals such as by the orthodontist to adjust resistance with the embodiments. The collected data can be used to determine the amount of increased energy required to compress the device for chewing. Sensors 44, 46 can provide information about strength of the chewing muscles, the number of times the person has chewed and other relevant data for helping with weight loss.

The embodiments can be used with or without partial dentures with the device fitting behind the molars. This method of installation can avoid surgery as these devices can be removed like mouth guards and dentures.

The novel invention allows for minimal surgical intervention which is important. The convenient reversibility of the procedure is important for the safety of the subject. There is concern for safety of the procedure in people having oral disease such as gingivitis, arthritis of the temporomandibular joint, avascular necrosis of the jaw and other unhealthy conditions of the jaw.

With the invention there may be need for regular monitoring of the device by the dentists. The importance of hygiene of the device can be emphasized for safety.

The use of the device can be attached to partial dentures and does not require a surgical procedure. A removable device attached to partial dentures can be more hygienic. There would be less risk as there would not be need for anesthesia as required during the procedures for implanted devices. A possible disadvantage of these type of devices would be to give the person the option of removing the device during meals or forgetting to insert the device while eating. This would interfere with the weight loss.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A mouth insertion device for assisting in weight control, comprising:
   a first elastic band;
   a first upper strap;
   a first lower strap;
   the first elastic band adapted to be mounted in a back of a mouth between an upper jaw and a lower jaw, the first elastic band configured to be attached to a left upper molar by the first upper strap, and the first elastic band configured to be attached to a left lower molar by the first lower strap;
   a second elastic band;
   a second upper strap;
   a second lower strap;
   the second elastic band adapted to be mounted in the back of the mouth between the upper jaw and the lower jaw, the second elastic band configured to be attached to a right upper molar by the second upper strap, and the second elastic band configured to be attached to a right lower molar by the second lower strap, wherein the first and the second elastic straps are adapted for increasing resistance of the upper jaw and the lower jaw during chewing action;
   an upper left housing attached to the first upper strap;
   an upper left magnet mounted to a bottom of the upper left housing;
   a lower left housing attached to the first lower strap;
   a lower left magnet mounted to a top of the lower left housing, the upper left magnet and the lower left magnet having opposing forces to one another;
   an upper right housing attached to the second upper strap;
   an upper right magnet mounted to a bottom of the upper right housing;
   a lower right housing attached to the second lower strap;
   a lower right magnet mounted to a top of the lower right housing, the upper right magnet and the lower right magnet having opposing forces to one another, wherein the upper left magnet, the lower left magnet, the upper right magnet and the lower right magnet increase resistance between the upper jaw and the lower jaw during chewing action to control caloric intake of food to assist in weight control.

2. The mouth insertion device of claim 1, further comprising:
   a first shock absorber having an upper end attached to the first upper strap, and a second end attached to a lower left molar strap spaced from the first lower strap, the lower left molar strap configured to be attached to a left lower molar;
   a second shock absorber having an upper end attached to the second upper strap, and a second end attached to a lower right molar strap spaced from the second lower strap, the lower right molar strap configured to be attached a right lower molar.

3. The mouth insertion device of claim 2, wherein each of the first and the second shock absorbers includes:
   a telescoping piston.

4. The mouth insertion device of claim 3, further comprising:
   sensors mounted on the mouth insertion device for detecting strength and chewing frequency data, and for remotely transmitting the data to a remote location.

5. The mouth insertion device of claim 2, further comprising:
   sensors mounted on the mouth insertion device for detecting strength and chewing frequency data, and for remotely transmitting the data to a remote location.

6. The mouth insertion device of claim 1, further comprising:
   sensors mounted on the mouth insertion device for directly detecting strength and chewing frequency data, and for remotely transmitting the data to a remote location.

7. A method for assisting weight control, comprising the steps of:
   providing a first elastic band having a first end attached to an upper left strap, and a second end attached to a lower left strap;
   mounting the first end of the first elastic band to an upper left molar by the upper left strap;
   mounting the second end of the first elastic band to a lower left molar by the lower left strap;
   providing a second elastic band having a first end attached to an upper right strap, and a second end attached to a lower right strap;
   mounting the first end of the second elastic band to an upper right molar by the upper right strap;
   mounting the second end of the second elastic band to a lower right molar by the lower right strap;
   increasing resistance between an upper jaw and a lower jaw by the first elastic band and the second elastic band during chewing action to control caloric intake of food to assist in weight control;
   attaching an upper left housing to the upper left strap;
   mounting an upper left magnet to a bottom of the upper left housing;
   attaching a lower left housing to the lower left strap;
   mounting a lower left magnet to a top of the lower left housing, the upper left magnet and the lower left magnet having opposing forces to one another;
   attaching an upper right housing to the upper right strap;
   mounting an upper right magnet to a bottom of the upper right housing;
   attaching a lower right housing to the lower right strap;
   mounting a lower right magnet to a top of the lower right housing, the upper right magnet and the lower right magnet having opposing forces to one another; and
   increasing resistance during chewing with the upper left magnet, the lower left magnet, the upper right magnet and the lower right magnet.

8. The method of claim 7, further comprising the steps of:
   providing a first shock absorber having an upper end and a lower end with a telescoping piston therebetween;
   mounting the upper end of the shock absorber to the upper left strap;
   mounting the lower end of the shock absorber to a lower left molar strap;
   providing a second shock absorber having an upper end and a lower end with a telescoping piston therebetween;
   mounting the upper end of the second shock absorber to the upper right strap;
   mounting the lower end of the second shock absorber to a lower right molar strap; and
   increasing resistance between the upper jaw and the lower jaw with the first and the second shock absorbers during chewing action to control caloric intake of food to assist in weight control.

9. The method of claim 8, further comprising the steps of:
providing sensors for detecting strength and chewing frequency;
mounting the sensors adjacent to the upper left strap or the lower left strap or the upper right strap or the lower right strap; and
detecting strength and chewing frequency data directly from the sensors; and
remotely transmitting the data to a remote location.

10. The method of claim 7, further comprising the steps of:
providing sensors for detecting strength and chewing frequency;
mounting the sensors adjacent to the upper left strap or the lower left strap or the upper right strap or the lower right strap; and
detecting strength and chewing frequency data directly from the sensors; and
remotely transmitting the data to a remote location.

11. A mouth insertion device for assisting in weight control, comprising:
a first elastic band;
a first upper strap;
a first lower strap;
the first elastic band adapted to be mounted in a back of a mouth between an upper jaw and a lower jaw, the first elastic band configured to be attached to a left upper molar by the first upper strap, and the first elastic band configured to be attached to a left lower molar by the first lower strap;
a second elastic band;
a second upper strap;
a second lower strap;
the second elastic band adapted to be mounted in the back of the mouth between the upper jaw and the lower jaw, the second elastic band configured to be attached to a right upper molar by the second upper strap, and the second elastic band configured to be attached to a right lower molar by the second lower strap, wherein the first and the second elastic straps are adapted for increasing resistance of the upper jaw and the lower jaw during chewing action;
a first shock absorber having an upper end attached to the first upper strap, and a second end attached to a lower left molar strap spaced from the first lower strap, the lower left molar strap configured to be attached to a left lower molar;
and
a second shock absorber having an upper end attached to the second upper strap, and a second end attached to a lower right molar strap spaced from the second lower strap, the lower right molar strap configured to be attached a right lower molar, wherein the first and the second shock absorbers are adapted to further resist chewing action between the upper jaw and the lower jaw.

12. The mouth insertion device of claim 11, wherein each of the first and the second shock absorbers includes:
a telescoping piston.

13. The mouth insertion device of claim 12, further comprising:
sensors mounted on the mouth insertion device for directly detecting strength and chewing frequency data, and for remotely transmitting the data to a remote location.

14. The mouth insertion device of claim 11, further comprising:
sensors mounted on the mouth insertion device for directly detecting strength and chewing frequency data, and for remotely transmitting the data to a remote location.

* * * * *